(12) United States Patent
David et al.

(10) Patent No.: US 8,211,014 B2
(45) Date of Patent: Jul. 3, 2012

(54) CHAIR AND ANCILLARY APPARATUS WITH MEDICAL DIAGNOSTIC FEATURES IN A REMOTE HEALTH MONITORING SYSTEM

(75) Inventors: Daniel David, Ranana (IL); Zipora David, Ranana (IL); Irving Levy, Rishon LeZion (IL); Ziv Halperson, Ramat Gan (IL)

(73) Assignee: Commwell, Inc., Evanston, IL (US)

( * ) Notice: Subject to any disclaimer, the term of this patent is extended or adjusted under 35 U.S.C. 154(b) by 0 days.

(21) Appl. No.: 13/092,570

(22) Filed: Apr. 22, 2011

(65) Prior Publication Data

US 2011/0201907 A1    Aug. 18, 2011

Related U.S. Application Data

(63) Continuation of application No. 10/890,042, filed on Jul. 13, 2004, now abandoned, which is a continuation of application No. 10/276,455, filed as application No. PCT/US01/16360 on May 18, 2001, now Pat. No. 6,832,987.

(60) Provisional application No. 60/232,708, filed on Sep. 15, 2000, provisional application No. 60/205,369, filed on May 18, 2000, provisional application No. 60/205,144, filed on May 18, 2000.

(51) Int. Cl.
*A61B 5/00* (2006.01)
*A61B 19/00* (2006.01)
*A47B 97/00* (2006.01)

(52) U.S. Cl. ...... 600/300; 600/301; 128/897; 297/463.2

(58) Field of Classification Search .......................... None
See application file for complete search history.

(56) References Cited

U.S. PATENT DOCUMENTS

| | | | |
|---|---|---|---|
| 3,906,931 A | 9/1975 | Terekhov | |
| 4,195,643 A | 4/1980 | Pratt, Jr. | |
| 4,702,108 A | 10/1987 | Amundsen et al. | |
| 4,949,729 A | 8/1990 | Haski | |
| 5,210,706 A * | 5/1993 | Nishiyama | 702/41 |
| 5,299,454 A | 4/1994 | Fuglewicz et al. | |
| 5,331,549 A | 7/1994 | Crawford, Jr. | |
| 5,410,471 A | 4/1995 | Alyfuku et al. | |
| 5,511,571 A | 4/1996 | Adrezin et al. | |
| 5,544,649 A | 8/1996 | David et al. | |
| 5,620,003 A | 4/1997 | Sepponen | |

(Continued)

FOREIGN PATENT DOCUMENTS

EP    0760225    3/1997

(Continued)

OTHER PUBLICATIONS

European Search Report, dated Jan. 13, 2012, Application No. EP 11 19 4367.6.

(Continued)

*Primary Examiner* — Henry M Johnson, III
*Assistant Examiner* — Shirley Jian
(74) *Attorney, Agent, or Firm* — Banner & Witcoff, Ltd.

(57) ABSTRACT

A medical examination chair includes a group of sensors including electrodes in finger-tip sensors, various other types of sensors incorporated in straps for the patient in the chair and load cells supporting the chair, all of which provide data which is partially processed in the electronics mounted in the chair and then transmitted to a central station for patient diagnosis.

15 Claims, 8 Drawing Sheets

U.S. PATENT DOCUMENTS

| | | | |
|---|---|---|---|
| 5,861,582 A | 1/1999 | Flanagan et al. | |
| 5,885,231 A | 3/1999 | Cramer et al. | |
| 5,987,982 A | 11/1999 | Wenman et al. | |
| 6,009,764 A * | 1/2000 | Fukunaga | 73/862.193 |
| 6,063,046 A | 5/2000 | Allum | |
| 6,163,903 A | 12/2000 | Weismiller et al. | |
| 6,223,606 B1 * | 5/2001 | Burke et al. | 73/862.041 |
| 6,416,485 B1 | 7/2002 | Rovetta et al. | |
| 6,832,987 B2 | 12/2004 | David et al. | |
| 7,396,331 B2 * | 7/2008 | Mack et al. | 600/300 |
| 7,785,257 B2 * | 8/2010 | Mack et al. | 600/300 |
| 2003/0083587 A1 | 5/2003 | Ferek-Petric | |
| 2004/0082870 A1 | 4/2004 | Rudy et al. | |
| 2008/0077020 A1 * | 3/2008 | Young et al. | 600/484 |
| 2010/0210921 A1 * | 8/2010 | Park et al. | 600/301 |

FOREIGN PATENT DOCUMENTS

| | | |
|---|---|---|
| EP | 1074217 A1 | 2/2001 |
| WO | 91 01111 A | 2/1991 |
| WO | 98 34577 A | 8/1998 |
| WO | 98 52467 A | 11/1998 |

OTHER PUBLICATIONS

Francis, D.B. et al., "Compensating the VCG for Variations in Electrode Positions", Proceedings of the 20th Annual Conference of Engineering in Medicine and Biology, Nov. 13-16, 1967.

Sunemark, M. et al., "Serial VCG/ECG Analysis Using Neural Networks", Computers and Biomedical Research, Academic Press, London, vol. 31, Jan. 1, 1998, pp. 59-69.

* cited by examiner

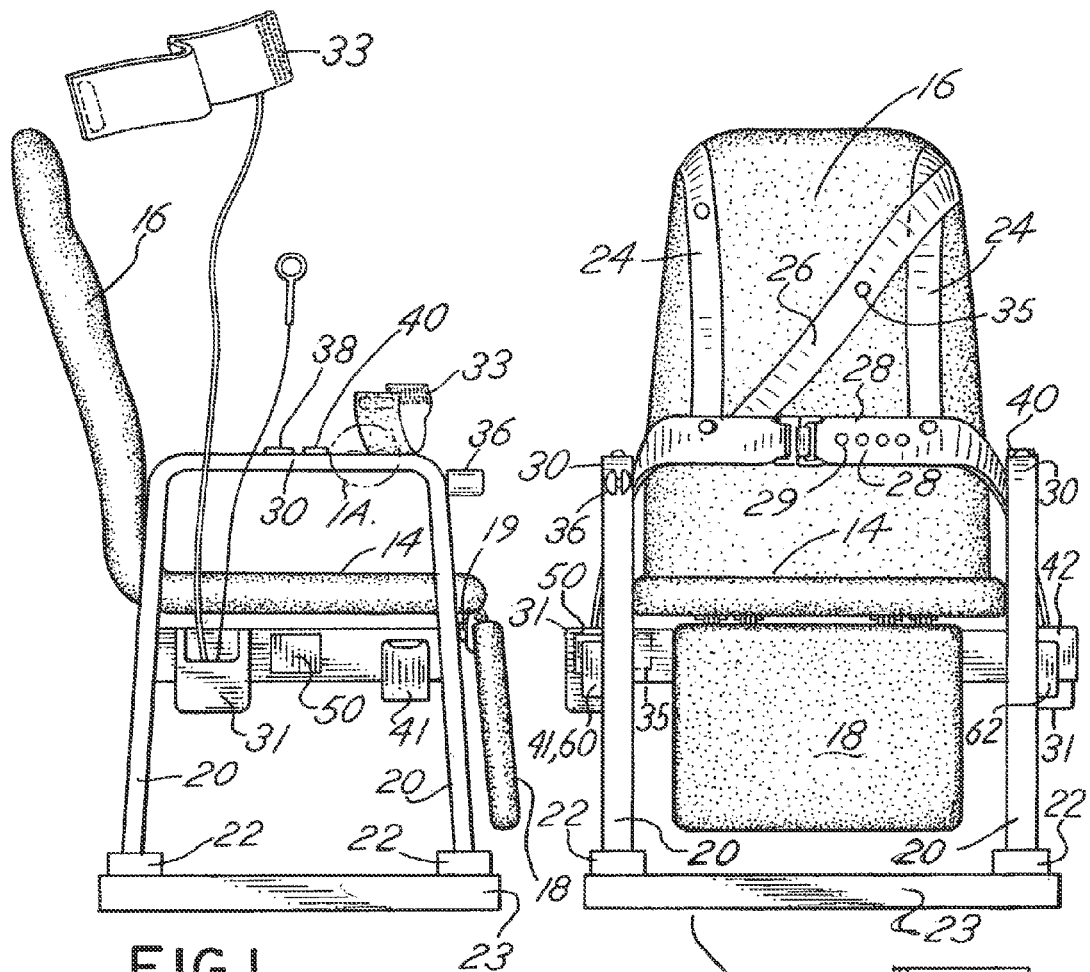
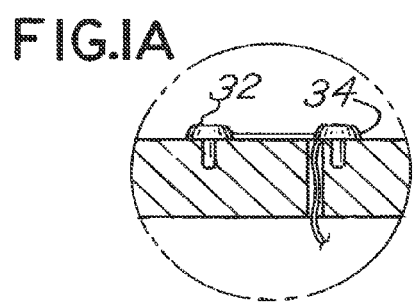
FIG.1
FIG.2
FIG.1A

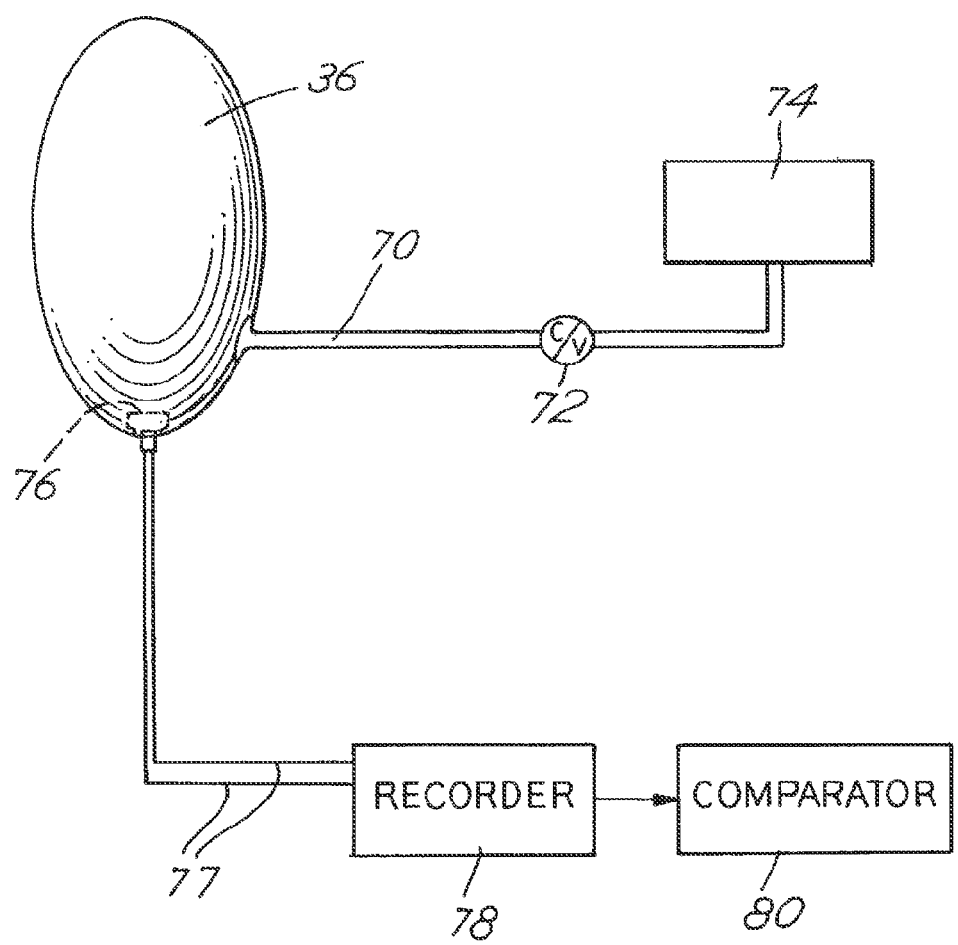

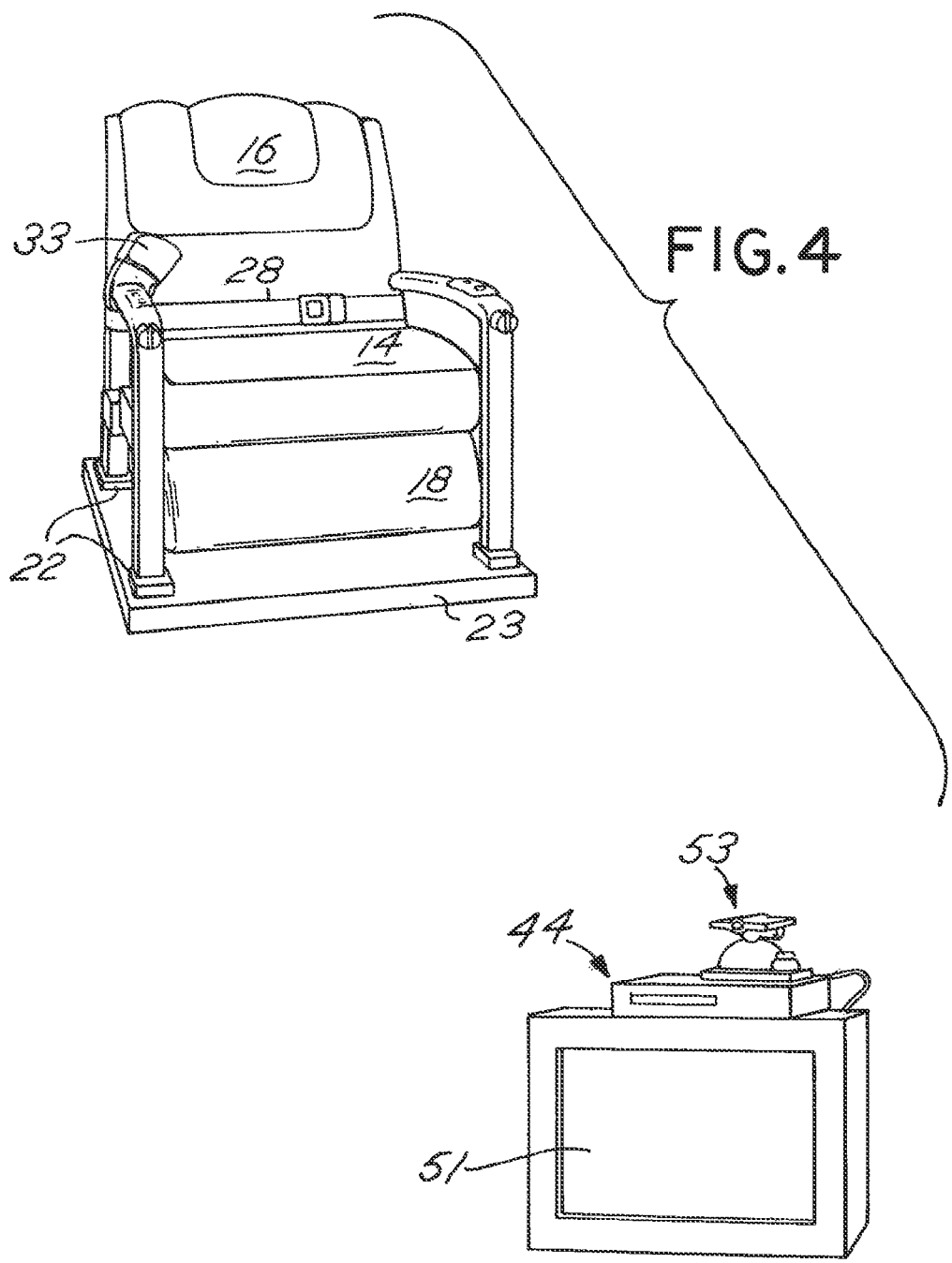

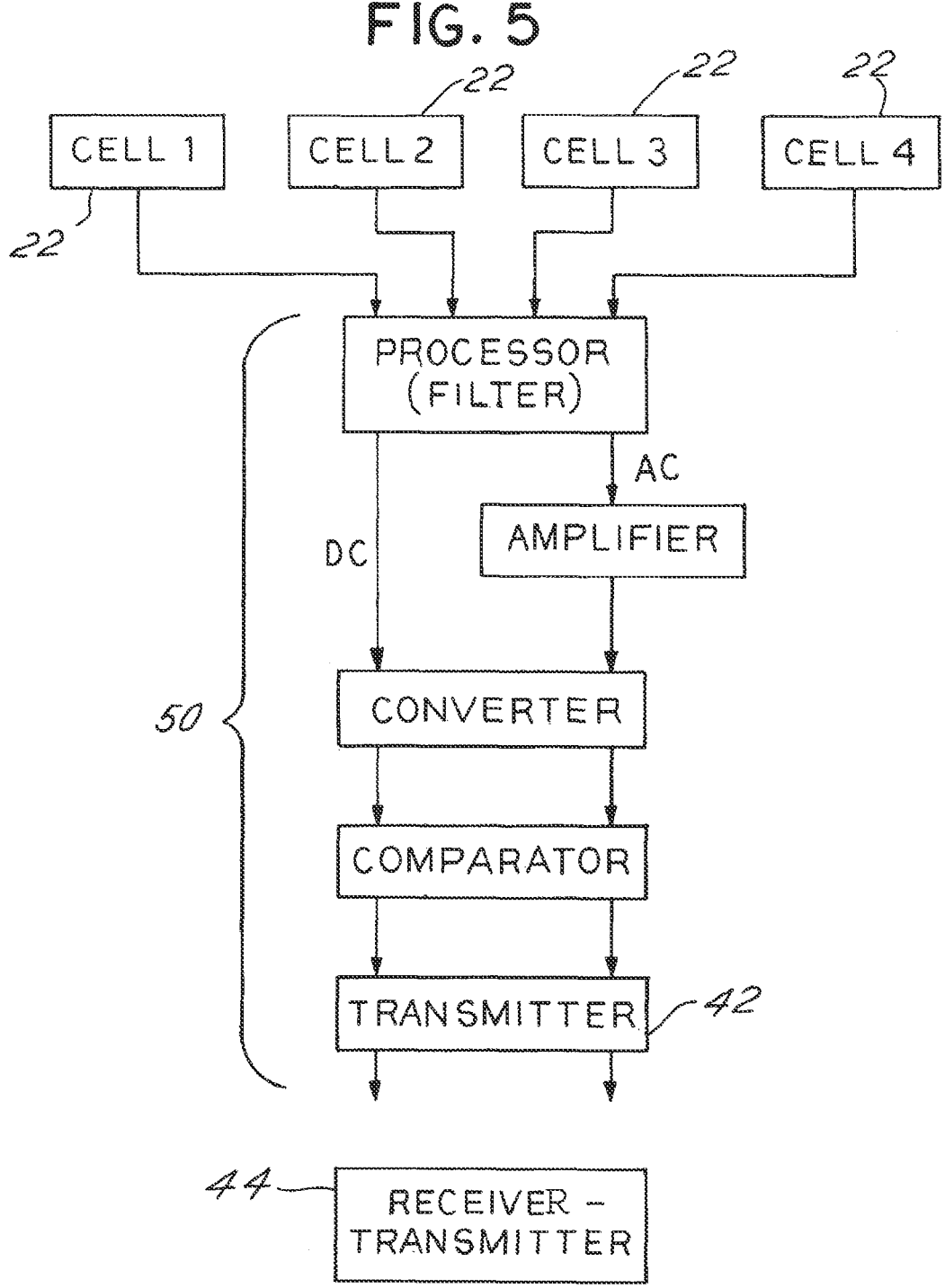

CHAIR AND ANCILLARY APPARATUS WITH MEDICAL DIAGNOSTIC FEATURES IN A REMOTE HEALTH MONITORING SYSTEM

CROSS REFERENCE TO RELATED APPLICATIONS

This is a continuation application of utility application Ser. No. 10/890,042 filed Jul. 13, 2004 now abandoned. Application Ser. No. 10/890,042 is a continuation application of utility application Ser. No. 10/276,455 filed Nov. 18, 2002 (now U.S. Pat. No. 6,832,987) which is based on PCT/US01/16360 filed May 18, 2001, which claims priority to and incorporates by reference the following three provisional applications: Ser. No. 60/232,708, filed Sept. 15, 2000, Ser. No. 60/205,369 filed May 18, 2000, and Ser. No. 60/205,144 filed May 18, 2000, upon which we claim priority.

BACKGROUND OF THE INVENTION

In a principal aspect, the present invention relates to a chair and ancillary apparatus incorporated with the chair for use in the conduct of medical diagnostic tests in a diagnostic system wherein the subject may be remotely located.

U.S. Pat. No. 5,544,649, incorporated herewith by reference, discloses various techniques for interactive patient monitoring from a central station, (e.g., a clinic) of patients located at a remote site, (e.g., their home). The diagnostic techniques disclosed in U.S. Pat. No. 5,544,649 rely, at least in part, upon utilization of apparatus, such as a diagnostic chair incorporating various sensor apparatus to facilitate the conduct of diagnostic measurements. U.S. Pat. No. 5,544,649 discloses a chair which includes sensors for measuring patient temperature, blood pressure and the like, and for transmitting such data via alternative transmission means to a central station for analysis and diagnosis.

The diagnostic session involving a patient in a remote location chair may be interactive. That is, the health care professional at the central station and the patient at the remote site are in real time, two-way audio and video communication and diagnostic data sensed at the remote location is simultaneously provided in real time to the central station. Such communication enhances the validity and the scope of the diagnostic tests being conducted.

The diagnostic information is analyzed by personnel at the central station. This provides a convenient and low cost manner in which to monitor patient condition without requiring the patient to physically travel to a diagnostic clinic or hospital. This technique and the associated apparatus also enable the health practitioner to direct the patient through test protocols and to diversify or revise the test protocols as necessary during the interactive session.

The use of apparatus of this type disclosed, and, in particular, a chair and various other ancillary equipment have become the topic of continued research and development in order to provide apparatus which senses the diagnostic parameters necessary to provide immediate and appropriate patient health care or monitoring in an inexpensive, yet highly reliable manner. Such continued research and development has led to the discovery of the apparatus disclosed hereinafter and also provides for the combination of such apparatus in an interactive diagnostic system.

SUMMARY OF THE INVENTION

Briefly, the present invention relates to the construction and design of a chair or other support platform device used for subject monitoring and medical examination and to the combination of such a device with a system for remote monitoring from a central station.

The device in the form of a chair or platform incorporates numerous apparatus for the acquisition of physiological and other diagnostic parameters from a subject who is sitting in or lying on the device. In a preferred embodiment, a chair is utilized which accepts commands for the acquisition and analysis of diagnostic data and sends the results, either processed on site and/or as raw data, by wireless communication to a relay system located at the site. The relay system then transfers data received from instrumentation incorporated in the chair to a central system by means of a wide bandwidth public channel (e.g., wireless network, telephone system, cable modem or other public utility). Communication and sensor control is interactive. That is, the transmissions are two-way transmissions. Additionally, two other communication channels are simultaneously operative, i.e., audio and video are interactive. Simultaneous, two-way transmission on three channels results in the capacity to diagnose and, to a limited extent, treat a patient at a remote site interactively. The channels may also be integrated for example by modulation or packing of a single channel signal.

By way of example and not limitation, the following medical information and testing, protocols are enabled by the chair or platform design: (1) finger-tip ECG, (2) "safety-belt" diagnostic ECG, (3) non-invasive blood pressure, (4) weight, (5) balance, (6) respiration rate, (7) saturated pulse oximetry (Sp02), (8) blood glucose analysis, (9) lung sounds, (10) expiratory flow (respiration exhale and/or inhale flow rates), (11) skin resistance, and (12) hand grip strength. All of the instrumentation required for the various measurements recited are an integral part of the chair. No special knowledge, expertise, or physical dexterity is required on the part of the patient or subject to participate in the test procedures since all of the instruments are an integral part of the chair or device. The chair also provides an ergonomically safe support for the patient, an aesthetically pleasant appearance and includes storage for the sensors and instruments not in use.

Exemplary of the diagnostic capabilities of the system and chair is measurement of hand grip strength of a patient. That is, a hand grip instrument can detect whether the patient suffers from tremors when gripping an object and thus can be relied upon as a diagnostic tool to evaluate the health of a patient. Apparatus which provide information of this general nature also allows assessment of motor activity which is associated with neurological features or capacity of a patient as well as strength which is associated with the muscle characteristics of a patient. Such monitoring is capable of projecting the likelihood or impact of stroke, for example, and other patient abnormalities.

Thus, a hand grip monitoring device which, in one embodiment, includes a bladder in the form of an elongated ellipsoid may be provided. A source of pressurized fluid is provided to the bladder with a check valve connected to the bladder filled with a predetermined volume of fluid (e.g., gas or liquid). A sensor is connected to the bladder for monitoring the fluid pressure in the bladder and providing a first signal which represents the absolute pressure therein and a second signal representative of the change in pressure over time. A recorder is provided for recording the first and second signals. Data associated with the first and second signals is analyzed, the first signal being representative of the total energy associated with patient grip and the second signal associated with tremors or a change in pressure with time. As indicated heretofore, tremors may be indicative of neurological status, neuromuscular pathology or stroke. The system may include historical recordings of like signals or a library of data to compare with the measurement or sensed signals in order to determine the change in patient health with time. Alarms may be provided to alert the medical technician at the central station of deviation beyond the general patient specific norm.

Another example involves load cells mounted on the support legs of the chair or device. The cells detect shifts in weight which, in turn, can be relied upon to diagnose balance and other physiological characteristics of a patient.

The chair and its associated diagnostic sensors may be utilized in combination with a remote monitoring system or infrastructure which operates from a central station by communication techniques with multiple, remote sites.

It is an object of the invention to provide a diagnostic chair or device and other ancillary apparatus used in combination with the chair to provide sensors that reliable interact with a patient for the measurement of respiration rate, pulmonary condition, heart condition, muscle strength, blood pressure, and other physiological parameters.

Yet a further object of the invention is to provide a highly reliable, yet inexpensive diagnostic apparatus comprised of a chair or furniture which may be utilized at a remote location yet easily transported from one location to another and easily interfaced with sensor transmission equipment and with a remote diagnostic system of the type generally depicted in U.S. Pat. No. 5,544,649.

Another object of the invention is to provide a chair or platform which maybe utilized to obtain diagnostic data from subjects located at a remote site for transmission to and recordal at a central station in order to obtain an historic record of the subject indicative of the wellness or deterioration in wellness of the subject or the status of recovery of the subject.

These and other objects, advantages and features of the invention will be set forth in the detailed description which follows.

BRIEF DESCRIPTION OF THE DRAWING

In the detailed description which follows, reference will be made to the drawing comprised of the following figures:

FIG. 1 is a side elevation of an embodiment of a chair with sensing apparatus;

FIG. 1a is an exploded sectional view of a portion of the chair depicted in FIG. 1;

FIG. 2 is a front elevation of the chair and ancillary apparatus of FIG. 1;

FIG. 3 is a schematic view of a hand grip sensor utilized in combination with the chair of the invention and with the system incorporating the chair;

FIG. 4 is a diagrammatic view of the diagnostic chair incorporated in a remote monitoring system;

FIG. 5 is a block diagram of the signal processing protocol for the load cells associated with measurement of weight, balance, respiration rate and other physical characteristics of a subject;

DESCRIPTION OF THE PREFERRED EMBODIMENT

Figure 6:
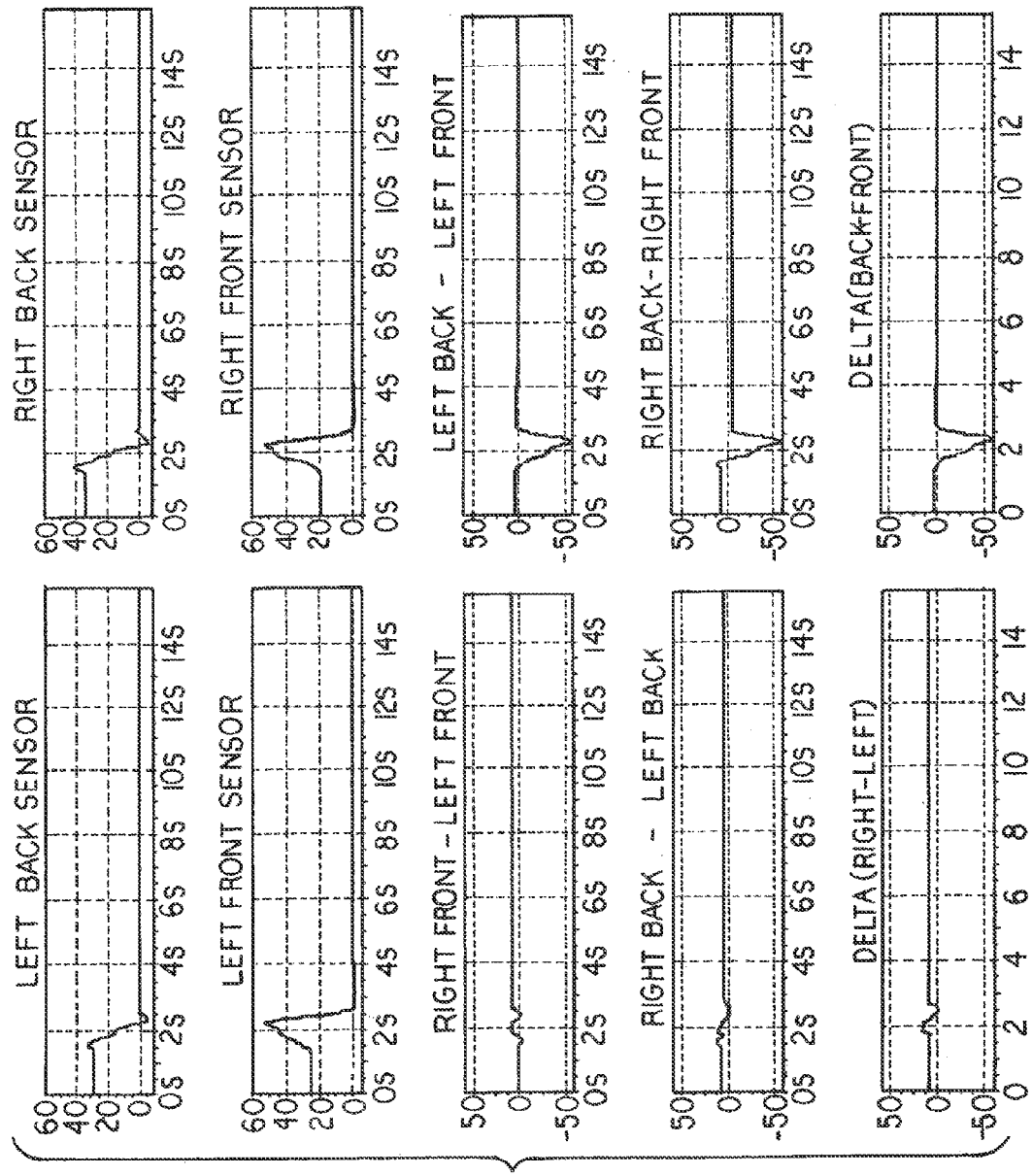
FIG. 6 is a series of graphs depicting the readings from load cells on a time scale and further depicting readings which represent the sum of various combinations of signals.

The apparatus of the invention comprises the combination of a chair or equivalent subject support platform device such as a bed, gurney or the like with various data, audio and visual transmission components. Thus, the chair depicted in FIGS. 1 and 2, involves data sensing, collection and transmission, as well as control of sensors in the chair through the data transmission links or channels. The chair typically comprises an element of an overall system and has self-contained sensing and control elements. FIG. 4 illustrates the chair and home unit components of such a system and the invention is described in the embodiment of a chair though other platform devices may be substituted such as a bed.

Referring to the figures, an exemplary chair includes the following elements: a seat 14, a back support 16 and an optional moveable, cantilever leg support 18. The chair is mounted on four, spaced legs 20 or the equivalent four mounting pads on the bottom of a chair base. Each leg 20 or mounting pad is supported on a separate load cell 22. A stable platform 23 supports the four load cells 22. The load cells 22 on fixed support platform 23 are used to measure or indicate weight, balance, and weight distribution at any given time and as a function of time as described in more detail below. The load cells 22 preferably are positioned on the corners of a rectangle.

Back support 16 includes an array of straps 24, 26, 28 and a non-invasive blood pressure cuff strap 33. Strap 26 is an electronic stethoscope strap 26 used for assessment of heart and lung sounds and includes a respirometer used for measuring respiration data. A "safety belt" like strap 28 is used for diagnostic ECG (electrocardiogram). The "safety belt" like strap 28 is similar to the design of a safety belt used in an automobile with attached electrodes 29 to permit secure placement of the electrodes 29 in the appropriate position on a human subject for obtaining a diagnostic single, multiple or full 12 lead ECG measurement. Ancillary electrodes 29 may be provided on the other straps 24, 26.

Moveable, cantilever leg support 18 facilitates raising the legs of a patient from resting on the floor when measuring patient weight by load cells 22. A strain gage 19 in leg support 18 also allows measurement of leg muscle strength. That is, a patient may attempt to lower the support 18 by engagement with their legs. The force imparted on support 18 by such activity may be sensed by a strain gage 19 to thereby provide a measurement of leg strength, muscle condition and muscle coordination.

Arm rests or supports 30 include "finger-tip" electrodes 32, 34 used for measuring a single lead ECG lead-I and skin resistance. A hand-grip 36 is used to measure hand muscular strength and control. A skin sensor 38 is used to measure blood glucose measurements. An infra-red emitter and sensor 40 is used to measure SpO2. An infra-red (IR) transmitter and receiver 42 is used for wireless communication to a transmission device 44 located at the patient or remote site. Communication device 44 is then linked to a central station, for example, by a wireless transmission, switched network cable line, telecommunication line or the like. An electronics enclosure 50 is attached underneath the seat 14 and contains the analog to digital conversion and microprocessor electronics for the operation of the sensor instruments in the chair.

The chair is designed so that the entire weight of the person sitting in the chair is transferred solely to the load cells 22. Thus, rectangular platform or frame 23 holds four load cells 22 arranged at the corners of the rectangular platform 23 supporting the chair. The frame 23 provides a means for physically locating the load cells 22 for supporting the chair. The frame 23 allows the load cells 22 to be fixed in each of the four corners of the rectangle or in any other desired geometric pattern associated with the legs 20 or chair support and the diagnostic protocol. Electronics which provide a common reference voltage to all load cells 22; differential amplifiers which amplify the temporal changes due to the weight shift on each load cell 22; bandpass filter for respiratory monitoring; low pass filter for human balance monitoring and a microprocessor with a multi-channel analog to digital converter are all housed in the enclosure 50. Software which controls data collection and signal processing is also incorporated in the hardware in the enclosure 50. Though the four load cells 22 are in a rectangular array, additional load cells in other arrays may be utilized to measure weight distribution as it varies with time over the surface of the seat 14 to thereby permit diagnostic measurements of the type discussed hereinafter. Each of the cells 22 provide a separate, recordable signal to the processing equipment described for ultimate transmission to a central station.

Respiration Rate Measurement

As previously described, a recliner chair is preferably used in order that support 18 will lift the feet of the patient from the floor. This is done so that all of the body weight of the patient is supported solely by the chair and the weight is directed in some pattern of distribution to each of the four sensors or load cells 22 under the chair seat 14 during measurement of respiration and other indices of patient health. That is, as a patient breathes, there is a small shift of weight from the back to the front of the chair or vice versa. This weight shift is transferred to the appropriate front and back load cells 22 in response to the shifting of patient weight due to respiration. The load cells 22 are thus arranged such that they can detect small changes in load due to patient respiratory induced weight shift. In other words, the load cells 22 are arranged so that they can detect load changes in both the X and Y directions, i.e., side to side and front to back of seat 14. As schematically depicted in FIG. 5, a high pass filter may be used to remove the DC component of the weight signal allowing only the AC changes in the signal to be passed. Since the AC changes are very small compared with the DC component, AC coupling allows the signal to be highly amplified. The signal to noise response of the system is improved by the quadrature nature of the signals. The quadrature nature of the signals arises from the fact that any increase in weight in one direction in the X-Y plane is compensated by an equal decrease in weight in the opposing direction in the X-Y plane. Noise and non-body movement artifacts thus can be removed from the signal. The front to back and side to side signal change of a sitting or recumbent subject represents respiration rate and many other physical parameters. In other words, by appropriately positioning load cells 22 and processing the AC component associated with changes in weight distribution, the system enables a physician or diagnostician located at a remote site to monitor respiration rate of the patient in real time responsive, for example, to instructed as well as natural breathing patterns. For example, the patient may have exercised before sitting in the diagnostic chair thereby enabling the diagnostician the opportunity to evaluate respiration rate following activity as well as at rest. Many variable patterns of patient activity are possible, all of which may be remotely monitored using the described system.

Weight

The lower portion of the chair acts as a scale that allows measurement of the gross weight of the patient sitting in the seat 14 of the chair. To measure total weight, the patient must raise his or her feet from the floor allowing all of the body weight to fall on the seat 14 of the chair. The DC component of the load cells signal is indicative of weight. Note, the chair may not include the cantilever leg support 18 in which event the patient must lift his or her legs from the floor to provide a true DC weight signal by the load cells 22. Also if the platform is a bed on gurney, then positioning of cells 22 will be dependent on the size of the platform and the platform will normally be supportive of leg or limb weight.

Balance

Each individual who sits down in the chair or gets up from the chair produces a characteristic response signature of time dependent weight distribution on each of the four load cells 22. The signature is used for historical reference to determine if changes in this signature may indicate physiological or pathological trauma as suggested, for example, by a change in patient ability to balance and in the response time to the command to change position (e.g., to rise from the chair) following instructions.

The monitoring of balance is accomplished by recording, for example, the transient response on the load cells 22 as a patient rises from the chair. The transient response provides a characteristic picture signature of the shifts of body weight as a function of time when the patient rises. For example, the weight is initially transferred from the back to the front of the chair and then later to the arms 30 which provide support for the person rising from the chair. Information from the four load cells 22 over time provides a characteristic picture signature of temporal balance changes as one rises from the chair. An example of data provided for diagnostic analysis includes measurement of the movement of the center of mass of a patient over seat 14 in the X and Y directions as a function of time. Unlike respiration, the weight signals relating to changes in balance and gross weight are large signals containing the DC element. The system is designed so that the characteristic frequency of the load cells 22 is well above the upper frequency response required from the system.

Periodic monitoring of a person rising from the chair produces data pattern signatures. These patterns are stored and statistically compared to new data using multidimensional statistical analysis. When the new data pattern signature is significantly different than the stored data pattern, an alarm (not shown) may be activated indicating the need for further diagnostic investigation. That alarm may be in the chair, but more appropriately is maintained at the diagnostic center.

In summary, the load cells 22 generate a myriad of data, including weight or load change as a function of time for each cell 22 as well as gross load for each cell 22 as a function of time. Preferably, this data is collected in its most basic form as analog signals by sensors 22. The signals are then typically converted to digital form by the software and hardware in the chair and transmitted by a wireless transmitter 42 to a receiver 44 at the remote site. There receiver 44 may store the data, compress the data and otherwise preliminarily process the data and subsequently forward the data via a preferred network, for example, to the central station. The data transmission may be interspersed with data or control signals to the transmitter 44. The data may thus be downloaded periodically or continually and may be processed, in part before transmission or transmitted in full.

The load cell 22 signals may be assigned to a single channel for transmission to the central station separate from the other diagnostic signals so that the interrelationship of the various diagnostic protocols may be observed. For example, weight shift data and gross weight data may interrelate with heart rate data to provide diagnostic insight. Consequently, assigning weight or load cell information to one data channel and heart rate and condition to another data channel may be optionally desired and programmed. Other diagnostic information may also be simultaneously recorded or sensed and then correlated with heart, weight distribution data, etc. Of course simultaneous audio and video interaction may also occur to facilitate the diagnostic activity.

FIGS. 6 through 9 are graphical results derived from load cell measurements of the direct current (weight parameter) of the load cells 22 in an experiment conducted to evaluate the diagnostic capacity of the device. The load cells were placed in a rectangular array with left and right back sensors or load cells 22 attached to the back legs or back edge of the chair and left and right sensors or load cells 22 attached to with the left and right front legs or front edge of the chair. Each figure depicts ten graphs which are the result of the processing of the signals from the four load cells 22. The first four graphs in the upper portion of each figure comprise or specify the absolute weights sensed by each of the sensors 22 taken during 2 second intervals. The next four graphs show differences between the pairs of adjacent sensors as indicated on the figure. The final two graphs show the summed differences of the back, the front, and of the left to right sensors, and are indicated as delta right to left and delta back to front.

Referring first to FIG. 6 there is depicted the results with respect to a person in good general health without handicap arising from a chair in a very normal fashion. The weight of a person arising from the chair is initially shifted from the back (as sensed by the change detected by the back sensors) to the front of the chair (as detected by the front sensors) causing the rise in signal and thus the rise in weight detected in the front sensors and a corresponding decrease in the weight detected in the back sensors. Once the person has risen from the chair, of course both the front and the back sensors show a decrease and a steady state with respect to weight. In FIG. 6 it is seen that the person is risen from the chair at approximately one second. Also it is to be noted that the differential weight shift from the front to the back indicates very little difference between the left to the right sides. This indicates that the person rose from the chair in a symmetrical manner. This suggests that muscle strength and coordination is balanced and that the person rose from the chair in a normal balanced fashion relying upon the equal strength and agility with respect to muscles on both sides of the body.

Figure 7:
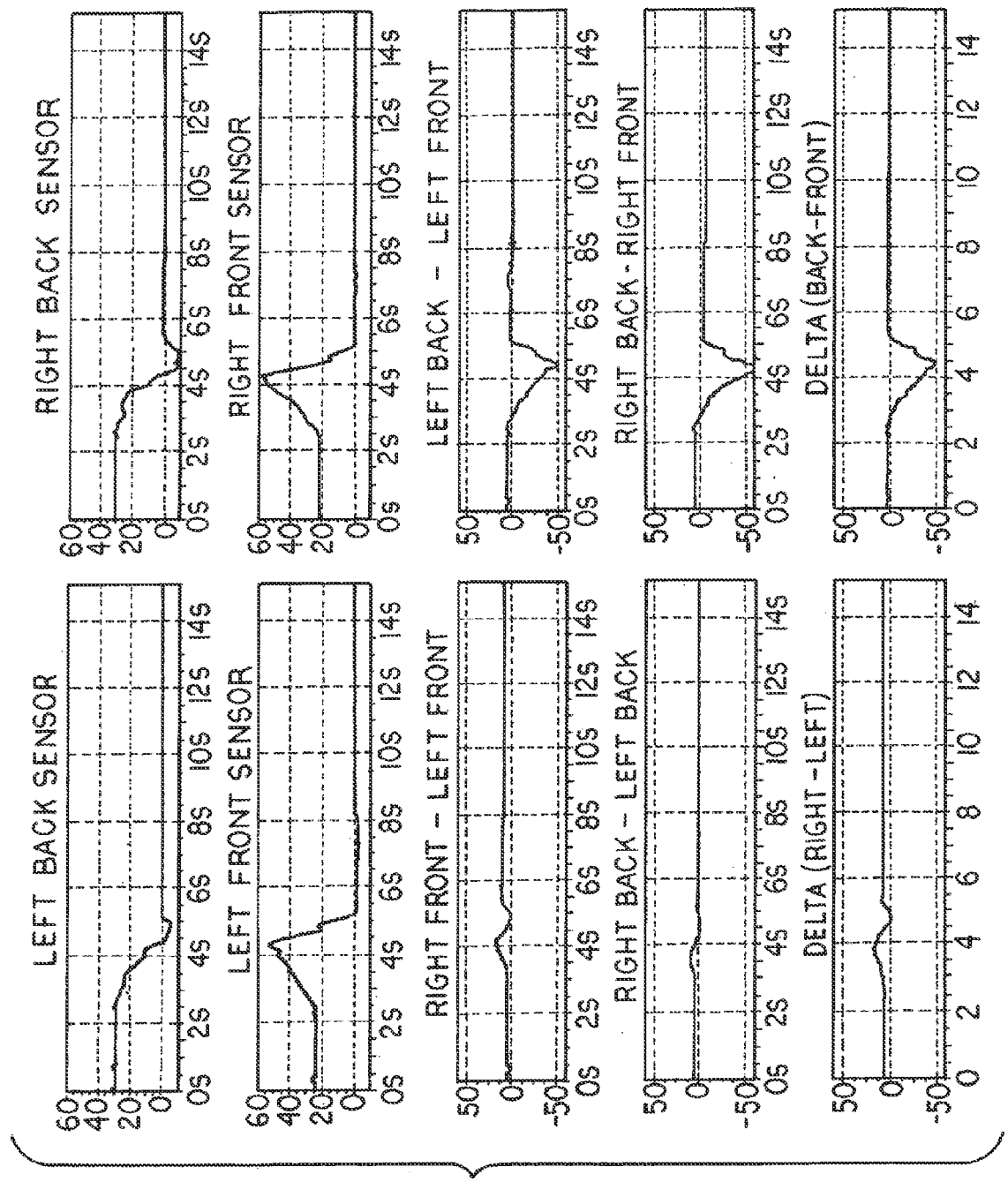
FIG. 7 is a series of graphs similar to FIG. 6 representing a distinct physiological pattern.

FIG. 7 includes graphs quite similar to those set forth in FIG. 6. However, the events required a longer time. Approximately two seconds are required to rise from a chair in the graphs depicted in FIG. 7. Again there is little difference between the left and right sensors during the event. Thus, though the person took almost twice as long, the person arose from the chair in a very symmetrical fashion. This indicates the balance of the person is symmetrical although because of the prolonged time to rise from the chair there may be an indication of weakness or diminished strength or some other indicator of a physiological problems.

Figure 8:
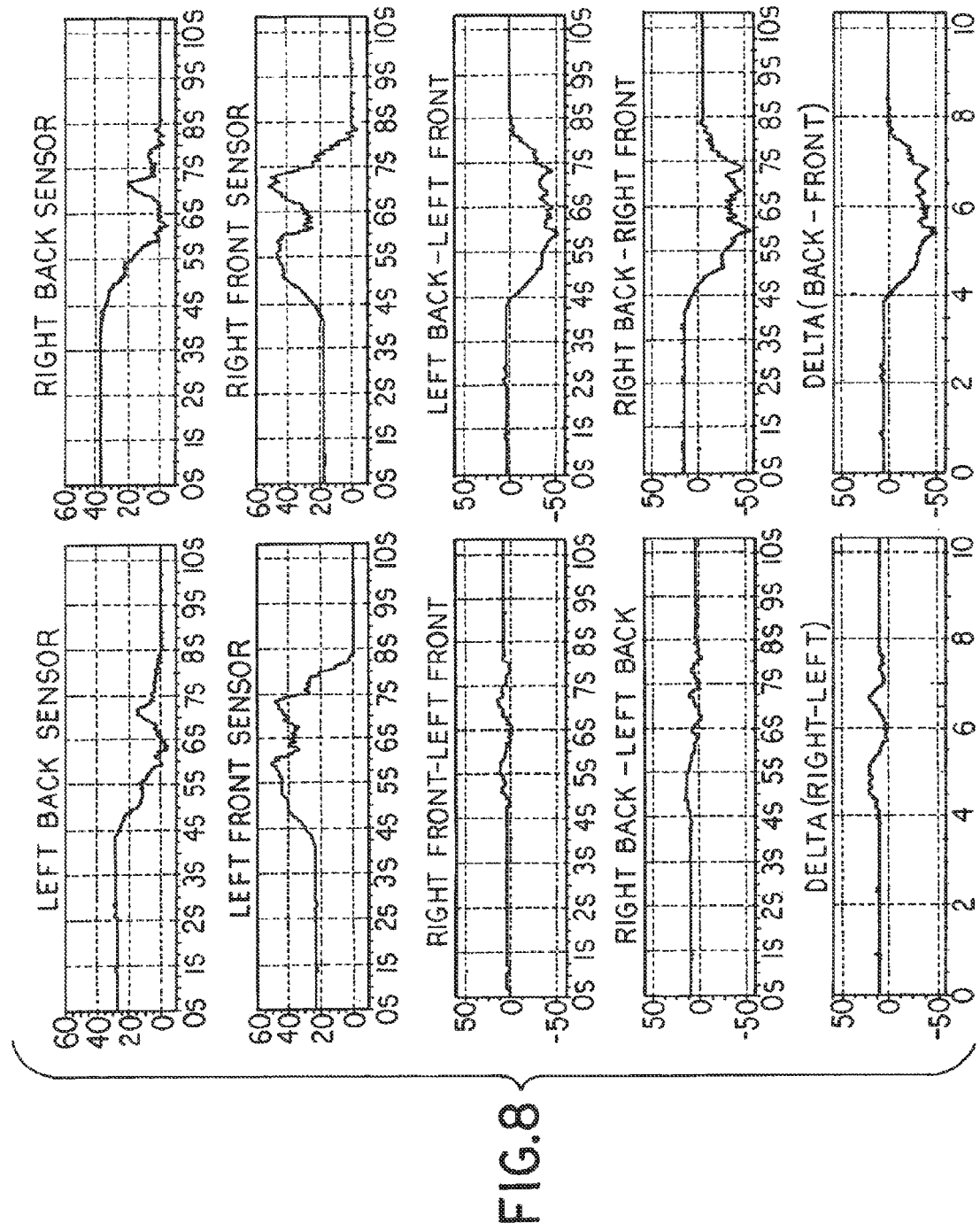
FIG. 8 is another series of graphs similar to FIG. 6 representing a further distinct physiological pattern.

FIG. 8 indicates a person rising slowly from a chair and then momentarily falling back into the chair before completely rising. The fact that the person fell back into the chair is indicated by the bimodal peaks in the graphs. However, in this circumstance the difference between the left and right sensors is still comparable indicating that the person rose in a symmetric fashion. These charts may indicate a loss of balance, a diminution or loss of muscle strength or other physiological problems, but in any event, suggest further diagnosis is in order.

Figure 9:
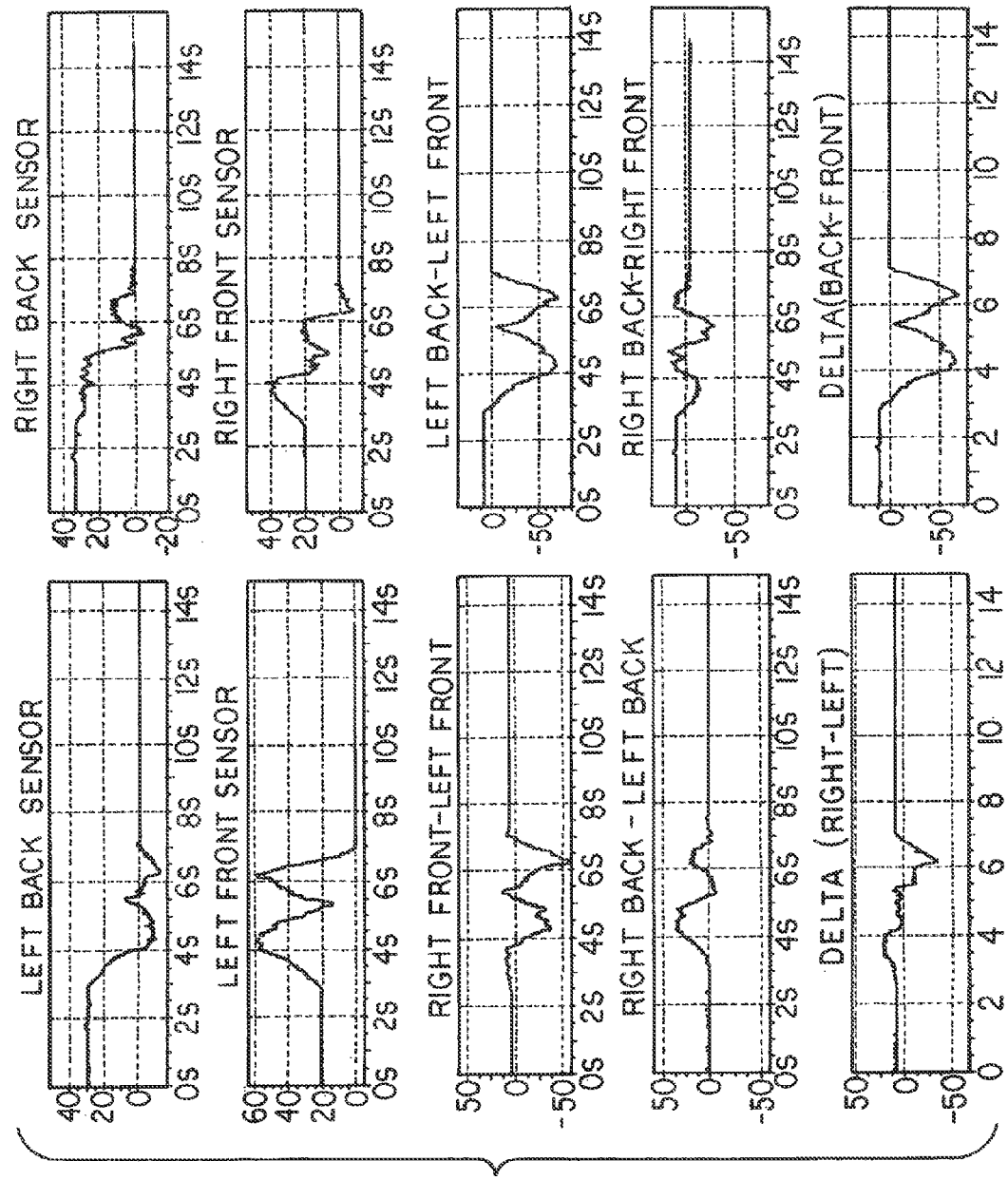
FIG. 9 is another series of graphs similar to FIG. 6 representing a further distinct physiological pattern or event.

FIG. 9 includes graphs or tracings that indicate that the person favors or leans to his or her left side. That is, the left side measurements increase while the right side measurements decrease. Otherwise, there is a shift from the back sensors to the front sensors as the person rises. The time period or term in order for the person to effect the movement is also somewhat prolonged. The pathophysiological indications from these charts suggest a weakness on the right side in muscle or muscle control or balance. Again, further testing and analysis are indicated.

Maintaining a record of such charts for a particular patient and comparing the charts over time will enable a practitioner to understand whether the person is maintaining a certain level of health, whether the patient is declining in health and whether, for example, therapy is assisting the patient with respect to recovery. Further charts along with norms associated with certain movements will facilitate the practitioners analysis and diagnosis.

Finger-Tip/Arm Rest ECG

Another type of data collected via the chair sensors relates to electrical sensing, most typically, ECG sensing. Thus, two electrodes 34, one mounted on the left arm 30 of the chair and one mounted in the right arm 30 of the chair, may be used to measure tile standard lead one ECG vector. The use of two electrodes 34 without a reference electrode is made possible by using an analog design incorporating a very high common mode rejection. The placement of the electrodes 34 is such that the measurement is made by the patient holding his or her arms and hands on both of the arms 30 of the chair simultaneously.

A second use of the two electrodes 34 is to provide a patient activated switch. Placing the fingers on the electrodes 34 provides one state of the switch, while removing the fingers from the electrodes 34 provides the second state of the switch. For example, the electrodes 34 of both arms 30 may require touching or activation to initiate a sequence of sensor operation. Consequently, initiation of the record of an ECG may not begin until the patient properly places fingers from each hand on separate sensors 34. Also, the patient may be required to operate the switches 34 in a sequence or in response to an audio or video signal to diagnose sight, sound, response time or memory or attention deficit.

Alternatively, for ECG monitoring, two electrodes 34 are placed on one arm 30 of the chair and a third electrode 34 (as a ground) is placed on the other arm 30 of the chair. The input from the two electrodes 34 on the same arm can then be monitored to provide for the vector one ECG reading or signal.

Multiple other variations of electrode positioning on the arms 30 and/or belts 24, 26, 28 are within the scope of the invention. For example, the sensors may be placed in the back support 16 of the chair. Such placement may incorporate redundancy inasmuch as multiple sensors may be provided to sense the same feature of patient health. For example, positioning of multiple electrodes 34 on each arm for engagement by separate digits of each hand can be utilized in combination with various prescribed video and audio instructions (either preprogrammed or initiated by the central station diagnostician). This may enable detection or analysis of muscular control, memory, attention span, etc. which, in turn, provide valuable diagnostic information for detection of disease such as stroke, Alzheimer disease, etc.

Safety Belt Diagnostic ECG

The "safety belt" is a diagnostic element which, in a preferred embodiment, consists of two portions, a chest strap 26 which crosses the patient's chest from the upper right to the lower left, and a lap portion 28 which crosses the patient horizontally above the abdomen from the right side to the left side where it meets with the chest strap 26. The straps 28, 26 are made with an elastic material allowing initial placement of electrode pads 29 to accommodate a patient's anatomy.

Electrode pods 29 are thus placed in the standard chest predefined positions used for the limb measurements of, LL and RL as well as the standard chest positions used for C1, C2, C3, C4, C5, and C6 of an ECG. The leads LA and RA are obtained from the finger-tip or arm rest electrodes 34. The elasticity of the belt strap 28 insures good skin contact while the measurement is made. When the measurement is completed the safety belt strap 28 returns into a housing 31 mounted on the side of the chair. A full 12 lead ECG consisting of leads 1, 11, 111, AVR, AVL, AVF, V1, V2, V3, V4, V5, V6 is derived from the input electrodes 29.

Alternative placement of electrodes is, as suggested above, possible. Thus, the number of electrodes, their placement, their structure and construction are variable depending upon the diagnostic protocol to be adapted.

Non-Invasive Blood Pressure

A cuff 33 is used to measure non-invasive blood pressure and is stored on the side of the chair. Cuff 33 is designed for easy placement on a patient's arm. The blood pressure measurement is activated remotely after the patient slides his arm into cuff 33. Electronics in the chair control enclosure or housing 50 automatically monitors inflation and deflation of the cuff. Sensors in cuff 33 detect pressure and pressure change. Measurement of blood pressure may be effected separately or simultaneously with other tests described. Again, a separate data channel coordinated with other channels may be utilized in the system. Also, the data may be gathered, processed, transmitted and analyzed in the manner described above for load cell data. Other alternatives for data storage and coordination with other parameters are possible again depending upon the diagnostic protocol adopted and typically controlled from the central station.

Saturated Pulse Oximetry

Pulse oximetry is a means to confirm the amount of oxygen in the blood. Standard instrumentation uses a comparison of absorption of red and infra-red light by the body tissue to determine the percentage of oxygenated blood cells by placing a finger clip emitter/sensor 40 on patient's finger. The chair incorporates a finger clip or socket 40 located in the arm 30 of the chair. The measurement will be made by the patient placing his finger in the finger clip or socket 40. A socket 40 may be provided in one or both arms 30. Again, the data may be processed as described above.

Blood Glucose Analysis

Blood glucose measurements are usually made by placing a drop of blood on a chemically treated paper and recording the color of the paper. The chair has an optical sensor 38 built into the arm 30 which can measure the color of the paper. In addition, a sterilized finger prick 60 using disposable finger pricks is built into the arm 30. A container 41 on the side of the chair is used to store finger pricks and paper, while another container 62 is used for disposing the used material. Alternatively, skin sensors can be attached to the chair to noninvasively measure blood glucose levels. The chair may also incorporate newer blood glucose measuring devices that do not require the drawing of a blood sample.

Heart and Lung Sounds

An electronic stethoscope is incorporated in strap 26 or may be attached to the side or back support 16 of the chair to assess heart and lung sounds. Alternatively, the stereoscope may be incorporated in belt or strap 26.

Respiratory Flow Measurements

A respirometer 35 attached to the side of the chair and is used to measure pulmonary inspiratory and expiratory flow functions. Respirometer 35 may be incorporated in strap 26.

Skin Resistance

Skin resistance is measured by placing a high frequency signal into the finger tip electrode 34 and measuring the associated resistance between the electrodes 34.

Manual Strength Measurement

Hand grips 36 placed on one or both arms 30 with sensors are used for early detection of neurological and neuromuscular dysfunction. The grips 36 measure the active force caused by muscular contraction as well as passive sensing of finger motion associated with tremors. Similar technology is built into the leg support 18 rest for the determination of leg muscle force.

Typically, referring to FIG. 3, one embodiment of a real time hand grip monitoring device comprises a bladder 36 in the form of an ellipsoid. However, other bladder shapes may be used which are comfortable for a patient to hold or grip. The bladder 36 may be positioned and incorporated in one arm 30 or two bladders 36 may be provided, one in each arm 30, i.e., for left hand gripping and for right hand gripping. A comparison of signals from both the left and right hand arrangement of bladders 36 is considered important when analyzing certain muscular and neuromuscular characteristics of a patient.

The bladder 36 is connected by a tube 70 through a check valve 72 to a fluid source 74. Typically, the fluid is air, although other fluids may be utilized. The bladder 36 further includes an internal pressure sensor 76 with sending leads 77 connected thereto. The sending leads 77 connect the sensor 76 with a data recorder 78. The data recorder 78 is connected with a data comparator 80.

Typically, the bladder 36 is maintained at atmospheric pressure. When there is no manual pressure applied to the bladder 36, then there is no pressure differential with respect to atmospheric pressure. Squeezing the bladder 36 increases the pressure within the bladder 36. This pressure is sensed by the pressure sensor 76. The pressure sensor 76 produces an electrical voltage proportional to the pressure applied to the sensor which varies in time, depending upon the patient's strength and grip. The voltage contains two elements, a direct current element and an alternating current element. The direct current element represents the absolute pressure while the alternating current element represents changes in pressure associated with physiological change, for example, information relating to muscle or hand tremors.

Thus, the signal from the sensor 76 is divided into two parallel processing paths. The first path is for the direct current signal. Typically, the path will have a filter that removes the AC or alternating current portion of the signal. The second path is for the alternating current portion of the signal. This path removes the direct current portion. In each instance, after removal of the appropriate portion of the signal, by virtue of an appropriate filter, the signal is amplified. The signals will then be converted into a digital format if desired and necessary by hardware and software in housing 50. The digital signals then may be transferred to a communication system as described above or processed on site and then transmitted.

In practice, it is desirable to have a bladder 36 associated with both the left hand and right hand of the patient so as to compare data with respect to both channels for the left hand and right hand side of the patient. The patient hand strength with respect to each hand provides additional physiological information, for example, associated with stroke and stroke patient recovery.

In any event, the direct current signal typically will increase to a steady state value upon manual gripping. The steady state value represents maximum hand strength. The length of time at that fixed value represents the time during which the patient can maintain the maximum hand grip force on the bladder. Integration of that fixed value represents the total energy exerted by the patient. The data is typically recorded for future comparison.

The alternating current signals are converted to an appropriate frequency where the data frequency and amplitude are recorded. Historical comparisons can then be made for the individual patient or by comparison to the standard formats or a standard library of information. Over time, the change in the readings on both channels can be determined. The differential readings with respect to left and right hand signal processing can also be determined. Thresholds can be set and an alarm can be provided which will indicate the crossing of a signal threshold. That may be indicative of a possible abnormality of the patient.

An alternative embodiment of the hand grip sensor includes a grip mechanism with load cell sensors in place of the bladder construction described. Other mechanical or electro-mechanical substitutes may be utilized to provide the AC and DC signals.

System Operation

Of course, the chair is capable of interactive use as part of a remote station/central station system as generally described in the aforementioned U.S. Pat. No. 5,544,649. However, the present invention incorporates not only sensor specific features associated with the chair, but also system features associated with the means and protocol for collecting, analyzing, transmitting, and processing data. Also, the interrelationship of the collected data is made possible for diagnostic implication. That is, conducting and measuring multiple physical parameters simultaneously at a remote site provides a better diagnostic overview of a patient and the described system permits such a diagnostic overview.

It is possible, however, to vary the function, elements and construction of the diagnostic chair and system with the chair. For example, the number of load cells 22 and their geometric array may be varied in order to enhance the data representative of factors such as weight, respiration, rate, balance, etc. Also, the chair or device may be utilized in a hospital or clinic and is not restricted to remote site use.

In operation, the patient is directed to sit in the chair and to follow a series of steps in desired and specific sequence or simultaneously. The directions are provided through the remote monitoring audio and video transmission from the central station. As depicted in FIG. 4, a video screen 51 and camera 53 are utilized in combination with the chair. As each instrument, for example, the straps 26, 28 are attached to the patient by the patient, a signal is initiated and transmitted from the transmitter receiver 42 to the transmission device 44 and then back to the central station. The electronics and logic systems in the electronics enclosure 50 control all of the initial sensing and set up and the described processing of the various signals from the patient. Thus, data manipulation is accomplished in the software and hardware and maintained in the chair or at the remote site as an initial first step. The essential data is then transmitted from the transmitter receiver to the transmission device and ultimately over some network such as a switched network to the central station. Upon completion of the examination, the patient will rise from the chair and disconnect the chair from a power source.

The platform may be in the form of a chair as described on in the form of a bed or gurney or other subject support device. Repositioning the sensors on various platforms is viewed as within the scope of the ability of a practitioner in the relevant field. The platform is also useful for detection of physical change, monitoring of subject wellness, emergency diagnosis, general health care management, rehabilitation monitoring, recovery monitoring, information collection, information dissemination, and interaction with respect to health and wellness for geriatrics especially Examples of the utility of the device include the following.

EXAMPLE 1

Congestive Heart Failure (CHF) Patients

Currently CHF patients present one of the biggest challenges of medicine. The New England Journal of Medicine reports that heart failure affects approximately 6 million Americans and is the leading cause of hospitalization for adults over the age of 65. Annual expenditures for heart failure related costs are estimated as high as $38 billion, according to research conducted by the Journal of the American College of Cardiologists, of which $23 billion is for hospitalizations.

Numerous studies suggest that comprehensive heart-failure-management programs can improve patients' quality of life, reduce hospital readmissions and emergency room visits and save overall costs of treating this condition. Despite the improved results, physicians are concerned about the low level of compliance. The lack of compliance results in inaccurate data received from patients with the consequence of inappropriate treatment. The present system and device permits transmission of data such as weight, ECG, balance and coordination information etc., from the patient site to the monitoring center which will be done automatically without the need of patient activity, audio-visual verification of medication in-take, and visual contact with a health practitioner to maintain human contact.

EXAMPLE 2

Diabetes

Diabetes affects 5.9% of the U.S. population, estimated to be 15.7 million Americans.

Approximately half of all diabetes occurs in people older than 55. Of the 65 and older population yearly 18.4% (6.8 million people have diabetes). Diabetes causes many serious complications, including blindness, heart disease and kidney failure. One in four patients with diabetes develops foot problems which require treatment. Sixty thousand amputations are performed on people with diabetes in the U.S. each year. Complications from diabetes costs the U.S. economy $45 billion each year, with an additional $47 billion attributed to indirect costs from diabetes-related disabilities.

Diabetes requires daily self management. Education, frequent monitoring and medication adjustments in the home setting with the disclosed device will help patients achieve better glucose and blood pressure control, thereby preventing or slowing the progression of diabetes complications, provide psychological support achieved by audio-visual interaction with a nurse, and provide the capability of monitoring and retrieving various vital signs (i.e., ECG, NIBP, weight) and clinical observations (i.e., wounds, swelling, etc.) and to prevent complications such as cardiac problems and circulatory problems leading to amputation, stroke, etc.

EXAMPLE 3

Parkinson's Disease

Parkinson's disease is a progressive disorder of the central nervous system affecting approximately 2 out of 1,000 people, and most often develops after age 50. It is one of the most common neurological disorders of the elderly. Treatment begun early in the disorder can slow progression of the disease.

The health care provider may be able to diagnose Parkinson's disease based on the symptoms and physical examination. However, the symptoms may be difficult to assess, particularly in the elderly. Some of these symptoms are: muscle rigidity, stiffness, difficult bending arms and legs, unstable, or slumped-over posture, loss of balance, gait changes, shuffling walk slow movements, difficulty beginning to walk, difficulty in initiating any voluntary movement, small steps followed by he need to run to maintain balance, freezing of movement when the movement is stopped, inability to resume movement, shaking and tremor, changes in facial expression.

Some of these symptoms are not specific to Parkinson and may be confused with other disorders that cause similar symptoms. For example, the posture changes may be similar to osteoporosis or other changes associated with aging. Lack of facial expression may be a sign of depression. The tremor may not appear when the person is sitting quietly with arms in the lap.

Untreated, the disorder progresses to total disability, often accompanied by general deterioration of all brain functions. It may result in an early death if untreated.

Treated, the disorder impairs people in varying ways. Most people respond (to some extent) to medications. The extent of symptom relief, and how long this control of symptoms lasts, is highly variable. The side effects of medications may be severe. The device with its response time test and the ability to detect and measure tremors will enable the early detection of the disease as well as the follow up of the efficacy of the medications.

The type and number of tests which can be implemented utilizing the chair or an alternative platform may be varied. All of the tests described need not be performed. Various additional tests may be incorporated into the chair using additional types of sensors. Also, the chair (device) may be automatically controlled from a remote (or near) station to automatically perform a series of tests without a nurse or professional guiding the subject. The system can therefore be programmed to conduct testing upon initiation by the subject of a predefined protocol. The test results will then be transmitted and/or recorded for later personal review. Thus, the subject matter of the invention is to be limited only by the following claims and equivalents thereof.

What is claimed is:

1. A medical examination diagnostic device comprising:
   a generally rectangular, horizontal chair seat for accommodation of a seated patient;
   at least four seat support members located respectively at the corners of a rectangle, said seat having a front edge and a back edge, two of said support members generally aligned with the back edge and two of said support members generally aligned with the front edge;
   an independent load sensor device located under each of said support members, each said load sensor device configured for detecting the load independently on each of the load sensors to provide a set of four independent data signals for medical diagnosis;
   means for collecting said independent data signals;
   a processor that measures and records the four signals independently as a function of time corresponding to a weight distribution of a patient sitting on the generally horizontal chair seat, said processor configured to provide an indication of each one of the four signals as a change characterized by a temporally sequential relationship among said four independent recorded data signals wherein said indication is selected from the group consisting of at least one of the following:
   a diagnostic respiration rate;
   a physiological trauma; and
   a pathological trauma;
   said processor including a processor element for providing a base reference signal for each of said load sensors, a differential amplifier to amplify changes in signal from said base signal for each of said load sensors, and a high pass filter to remove the DC component of each of said signals from said amplifier and a low pass filter to remove the AC component of each of said signals; and
   a hand grip monitoring device including:
      a first bladder;
      a tube connected to the first bladder;
      a source of pressurized fluid connected to the first bladder through the tube;
      a check valve that monitors the first bladder and tube filled with a volume of fluid;
      a first pressure sensor connected to the first bladder that measures the fluid pressure in the first bladder and provides a bladder pressure signal having a first (DC) signal component representative of the absolute pressure in the first bladder during a measured time increment and a second (AC) signal component representative of the change in pressure over said measured time increment in the first bladder, and
      said processor configured to measure and record the first pressure signal component over said measured increment of time and the second pressure signal component over said measured increment of time, said first pressure signal component being integrated and recorded, said second pressure signal component being recorded to provide frequency and amplitude over the said increment of time, wherein the processor processes the first and second signals to detect a tremor of the patient.

2. The device of claim 1 further including one or more supplemental sensor elements selected from the group consisting of:
   a blood pressure sensor;
   a pulse oximetry sensor;
   a sound sensor;
   a skin resistance sensor;
   a manual grip sensor;
   a fluid flow rate sensor;
   a glucometer.

3. The device of claim 1 further including a sensor element sensing the voltage associated with each of said load sensors independently and a bandpass filter filtering out select signals.

4. The device of claim 3 further including a signal processor processing the voltage signals from the independent load sensors to measure a differential signal between at least two pairs of load sensors.

5. The device of claim 1 further including recording means for historical recording of signals to provide an historical record and a comparator comparing the historical record with other recordings.

6. The device of claim 5 wherein the other recordings are derived from the same patient.

7. The device of claim 6 wherein the recordings are derived at least in part from a source of independent norms.

8. The device of claim 7 further including an alarm denoting the departure from a source of the other recordings.

9. The device of claim 1 in combination with a central station, said device maintained at a remote station, said stations being linked by two-way communications medium.

10. The device of claim 1 in combination with multiple remote station devices and a single central station and further including a control system monitoring each device.

11. The device of claim 1 wherein there is provided a control system monitoring a plurality of remote stations and further including a switch connecting a central station to each of said remote stations individually and sequentially.

12. The device of claim 1, further comprising:
a second bladder;
a second pressure sensor connected to the second bladder for measuring a corresponding fluid pressure in the second bladder and providing a corresponding signal representative of the second fluid pressure; and
the processor comparing the corresponding signal from the second bladder and the first and second signals from the first bladder.

13. The device of claim 1, further comprising:
the processor determining whether a detected tremor is indicative of a stroke.

14. The device of claim 1, further comprising:
the processor detecting load changes in the X and Y directions from the set of four independent data signals.

15. The device of claim 1, further comprising:
the processor determining whether a characteristic response signature of the weight distribution is indicative physiological or pathological trauma.

* * * * *